United States Patent [19]

Grassmann

[11] 4,090,079
[45] May 16, 1978

[54] MEDICAL EXAMINING APPARATUS FOR THE PRODUCTION OF TRANSVERSE SECTIONAL IMAGES

[75] Inventor: Peter Grassmann, Erlangen, Germany

[73] Assignee: Siemens Aktiengesellschaft, Berlin & Munich, Germany

[21] Appl. No.: 761,597

[22] Filed: Jan. 24, 1977

[30] Foreign Application Priority Data

Feb. 18, 1976 Germany .............................. 2606534

[51] Int. Cl.² .......................... A61B 6/00; A61B 6/02; G01N 23/00
[52] U.S. Cl. ............................... 250/360; 250/445 T; 250/491
[58] Field of Search ................ 250/360, 363 S, 445 T, 250/491

[56] References Cited

U.S. PATENT DOCUMENTS

| | | | |
|---|---|---|---|
| 3,867,634 | 2/1975 | Hounsfield | 250/360 |
| 3,974,388 | 8/1976 | Distler et al. | 250/445 T |
| 3,999,073 | 12/1976 | Hounsfield | 250/445 T |
| 4,034,224 | 7/1977 | Heavens et al. | 250/445 T |
| 4,049,968 | 9/1977 | Distler et al. | 250/445 T |
| 4,053,781 | 10/1977 | Hounsfield | 250/445 T |

*Primary Examiner*—Alfred E. Smith
*Assistant Examiner*—T. N. Grigsby

*Attorney, Agent, or Firm*—Hill, Gross, Simpson, Van Santen, Steadman, Chiara & Simpson

[57] ABSTRACT

A ray measuring arrangement for scanning of a selected transverse section is associated with a compensating body of tissue equivalent material having a patient-receiving through-aperture of size such that a patient may be moved into and through such aperture by means of motor driven patient supports at opposite longitudinal sides of the aperture. For cranial examination, a holder ring of tissue equivalent material is supported for longitudinal movement within the aperture of the compensating body, the holder having a position adjacent a patient support so that the motor drive can transport the patient longitudinally until the patient's head rests on an elastic contouring member of the holder. The contouring member is then filled with a suitable liquid so as to closely conform with the contour of the patient's head. Thereupon, further motorized drive of the patient support moves the patient and the holder longitudinally until the patient's head is correctly located for examination. The reverse process is followed so as to remove the patient from the operating position by the motorized drive, the patient thereby smoothly and comfortably being returned to the initial position on the patient's support. For whole body examination, the holder is readily removed from the aperture of the compensating body.

4 Claims, 5 Drawing Figures

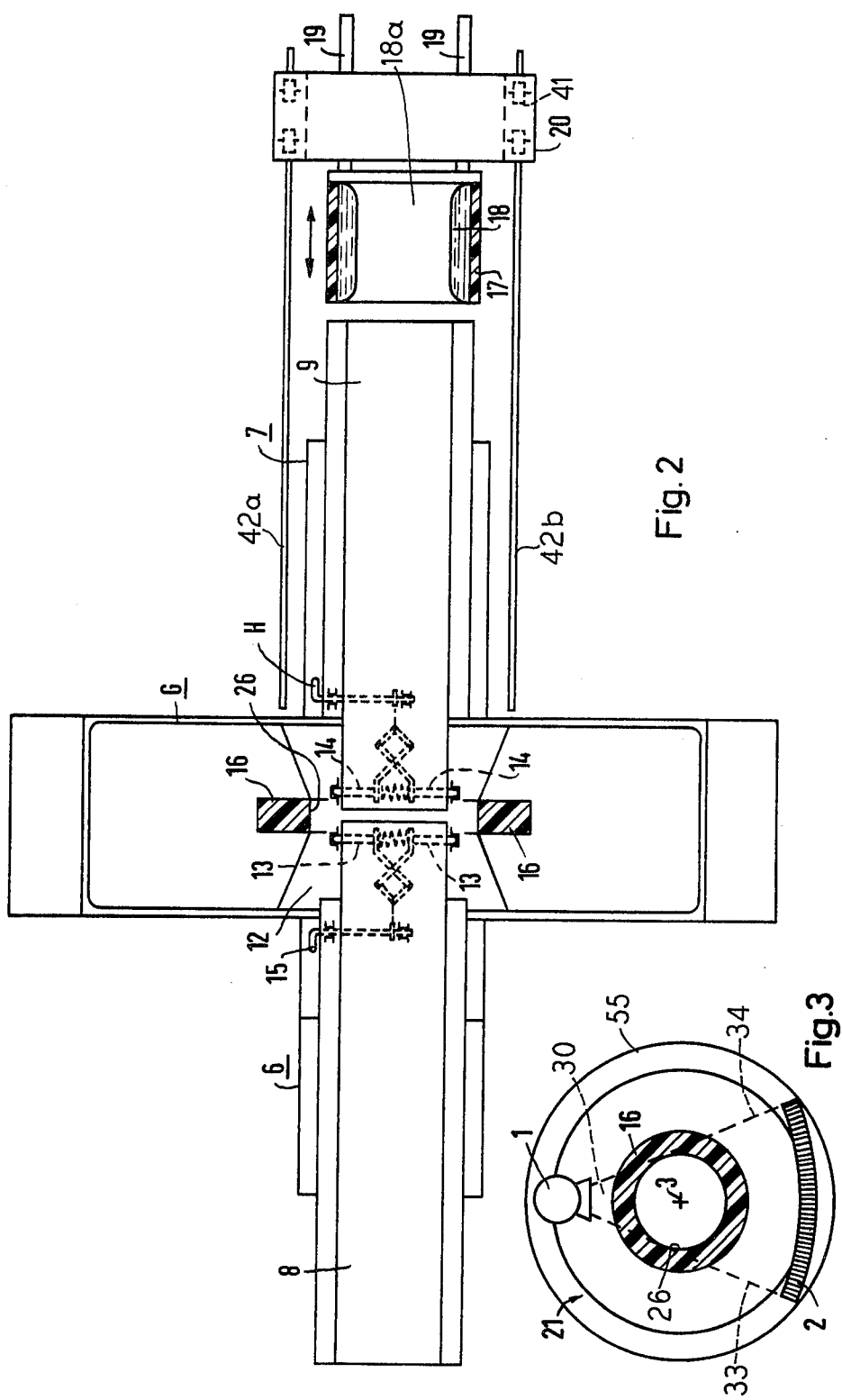

MEDICAL EXAMINING APPARATUS FOR THE PRODUCTION OF TRANSVERSE SECTIONAL IMAGES

BACKGROUND OF THE INVENTION

The invention relates to a medical examining apparatus for the production of transverse sectional images of an exposed object, comprising a ray measuring instrument including a ray source which generates a bundle of rays which penetrate the exposed object, and a radiation receiver which detects the radiation intensity beyond the object by detecting the projected bundle of rays. A driving device for the measuring instrument may comprise a pivot mounting for producing rotational movement of the measuring instrument, and a measurand converter may be provided for converting the signals supplied by the radiation receiver into a sectional image. The compensating body is interposed between the ray source and the radiation receiver and is made of tissue-equivalent material. This compensating body is provided with a patient-receiving through-aperture for enabling a patient to be introduced into the aperture and to be moved through the aperture as a desired transverse body segment is selected for examination.

For determining the sectional image, the rotational movements of the ray measuring instrument may take place through small equidistant angular amounts, each in alternating sequence with a displacement of the measuring arrangement along a straight line perpendicular to a central ray path of the ray beam when a single detector is employed as the radiation receiver. Alternatively, the displacements may be omitted if the ray receiver is built up of a multiplicity of ray detectors, the signals of which are simultaneously registered and processed by the measurand converter. In this case, an X-ray beam of a fan shape may be utilized with the X-ray energy simultaneously incident on all of the detectors which may be arranged in an arcuate array.

An X-ray apparatus of this general type is described in German OS No. 1,941,433. The path followed by the X-ray beam through the object to be examined is here longer at the center of the object to be exposed than in the peripheral regions, owing to the form of most objects which are exposed. Assuming that the object to be examined has constant density, different output signals are obtained from the radiation receiver during scanning which makes the processing of the measurand data difficult. In addition when a polychromatic ray spectrum is employed as is generally the case in medical X-ray diagnostic apparatus, it is found that, owing to varying attenuation of the X-ray beam due to the density differences within the body, the spectral composition of the radiation varies in dependence upon the attenuation. This makes the production of images very difficult.

In order to compensate for the attenuation differences produced between the cetral and peripheral regions owing to the form of the object exposed, it is known from the aforesaid publication to provide a compensating body consisting of tissue-equivalent material having an aperture for receiving the patient and to fill the space between the patient and the compensating body by a waterfilled bag. As this bag is filled, it bears against the outer surface of the patient and conforms to the body contour. In this way, it is ensured that the path of the radiation from its entrance into the compensating body until its exit therefrom is equal in all positions of the measuring arrangement and that, assuming that the object being examined is of constant density, the radiation is equally attenuated in each position of the measuring arrangement. In addition, the water pressure ensures that the patient is kept steady during examination.

SUMMARY OF THE INVENTION

The invention has for its object the provision of apparatus for medical examination and the like by means of which it is possible to carry out on the one hand whole-body examinations without the use of a water bag or similar contouring member, and on the other hand examinations of the cranium with the use of such a contouring member.

In accordance with the invention this object is achieved by virtue of the fact that the contouring member is mounted on a holder movably displaceable from the aperture of the measuring arrangement, and by virtue of the fact that the housing for the measuring arrangement and the holder with the contouring member are adapted to be moved in relation to one another in such a manner that the contouring member is precisely located so as to receive the head of the patient as the patient is moved toward the measurement location in a smooth and comfortable manner. With the subject of the invention, the patient support may be driven so as to position the head of the patient at the precisely desired location relative to the measuring arrangement, retain the patient's head at the desired location during examination, and then to comfortably and smoothly return the patient's head to the patient support.

Other objects, features and advantages of the invention will be apparent from the following detailed description taken in connection with the accompanying drawings.

BRIEF DESCRIPTION OF THE DRAWINGS

FIG. 2 is a similar somewhat diagrammatic plan view of the apparatus arranged as shown in FIG. 1 for the examination of a body segment of a patient;

FIG. 3 is a somewhat diagrammatic transverse sectional view on a reduced scale for the purpose of illustrating a preferred measurement arrangement with a fan-shaped X-ray beam and a multiplicity of detectors disposed in an arcuate array for simultaneous registration of the X-ray energy transmitted along a multiplicity of paths together covering the entire cross section of the patient-receiving through-aperture of the measuring arrangement;

DETAILED DESCRIPTION OF THE PREFERRED EMBODIMENT

Figure 1:
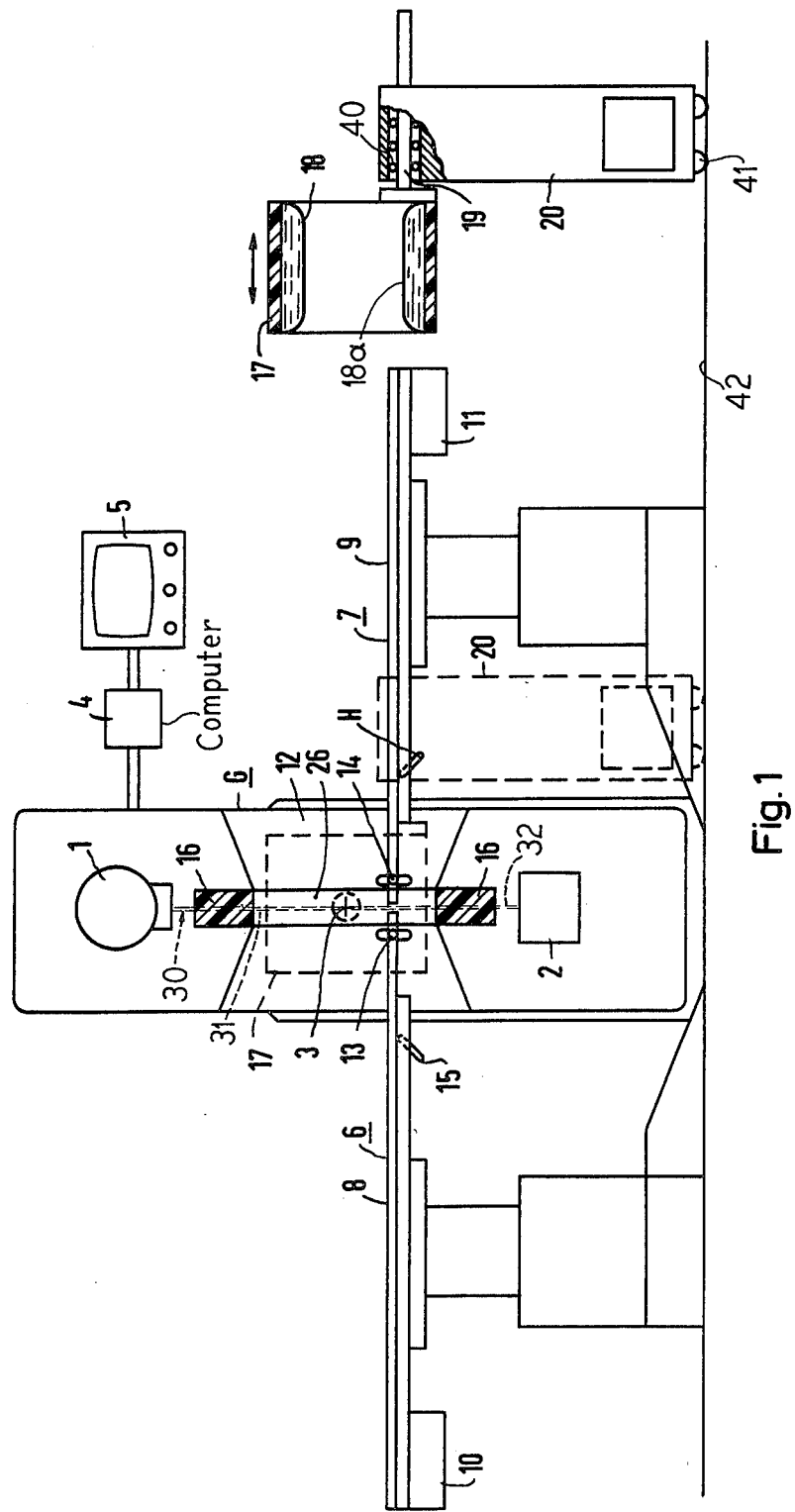
FIG. 1 is a side elevational view, somewhat diagrammatic in character, and illustrating apparatus according to the present invention arranged for examination of a body segment other than the head of a patient.

There is illustrated in FIG. 1 a housing G in which there is disposed a measuring arrangement comprising an X-ray tube 1 and a ray receiver 2. The measuring arrangement 1, 2 is adapted to be rotated in known manner about the patient, for example about a central point indicated at 3, so as to define successive sets of angularly offset ray paths intersecting a transverse section of the patient which is to be examined. The ray receiver 2 comprises a row of detectors as shown in FIG. 3 on which the fan-shaped bundle or beam 30 of X-ray energy from the X-ray tube 1 becomes incident. In the illustrated embodiment, the extent of the beam 30 in the longitudinal direction of the patient is indicated by marginal ray paths 31, 32 in FIG. 1, and represents the thickness of the body section being examined, while the beam of X-rays perpendicular to the plane of FIG. 1 has marginal rays as indicated by dash lines 33 and 34 in FIG. 3. As shown in FIG. 3, the angle of divergence between the outer ray paths 33 and 34 is sufficient to scan the entire patient-receiving cross section of the measuring arrangement so that an entire set of measurement data may be registered simultaneously in each angular position of the measurement means relative to the central point 3. Thus, by taking readings from the detectors 2 in each of 90 or more successive angular positions of the measurement arrangement about the central point 3, a sufficient number of sets of data are supplied to the computer 4 so as to define an image of the sectional plane under examination. This image may be displayed by means of a display unit 5 connected with the computer 4, for example.

During whole-body examinations, the patient is supported on two couches or patient supports 6, 7, which are covered by respective roll cloths 8 and 9. In transporting a patient from the patient support 6 into and through the receiving aperture, motors 10 and 11 drive the roll cloths 8 and 9 synchronously, so that the patient can be transported jointly by the patient supports 6 and 7 in the selection of the body section to be examined. Those ends of the two patient supports 6 and 7 which lie in the housing aperture 12 are anchored to the housing G by means of pins 13 and 14, operating in suitable slots in the housing as indicated diagrammatically in FIG. 2. For removing the patient supports 6 and 7 from the housing aperture 12, the pins 13 and 14 can be manually disengaged from the slots. FIG. 2 shows a lever 15 by which the pins 13 of the patient support 6 can be disengaged, and a similar lever H is indicated for disengaging the pins 14 of of the patient support 7. With the patient support 6 removed from the housing aperture 12, a patient can be conveniently placed on the roll cloth 8, whereupon the support 6 which may be upon suitable rollers or the like can be placed into the position shown in FIGS. 1 and 2 and locked in place by means of the pins 13.

Figure 5:
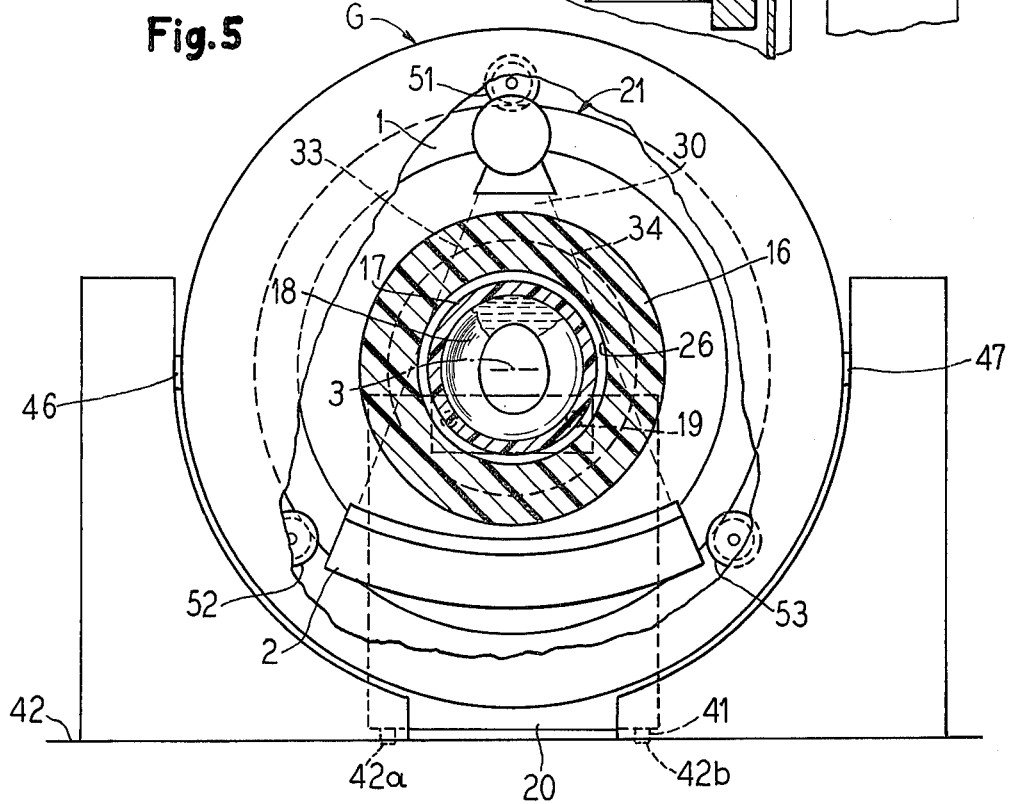
FIG. 5 is a somewhat diagrammatic partial transverse sectional view of the examining apparatus arranged as in FIG. 4.

Provided in the housing G between the X-ray tube 1 and the ray receiver 2 is a ring-shaped compensating body 16 consisting of tissue-equivalent plastic, which has the function of equalizing the attenuation along the successive ray paths over the extent of the beam as represented at 30 in FIGS. 3 and 5. The compensating body 16 has a patient-receiving through-aperture 26 of a size to accommodate the largest patient cross section for which the apparatus is designed. The extent of the beam 30 corresponds to the transverse extent of the aperture 26 as seen in FIG. 5 so that the measurement arrangement is also designed to accommodate such maximum patient cross section.

For carrying out an examination of the human cranium, there is provided a separately movable tissue-equivalent plastic ring 17 having an associated head-supporting contouring member 18. The plastic ring 17 is secured to two rods 19 which are so mounted on a support structure 20 as to be longitudinally displaceable in a smooth and relatively friction-free manner, for example by means of ball bearings 40. The support structure 20 has casters 41 for rolling support of the structure 20 on the floor level indicated at 42.

Figure 4:
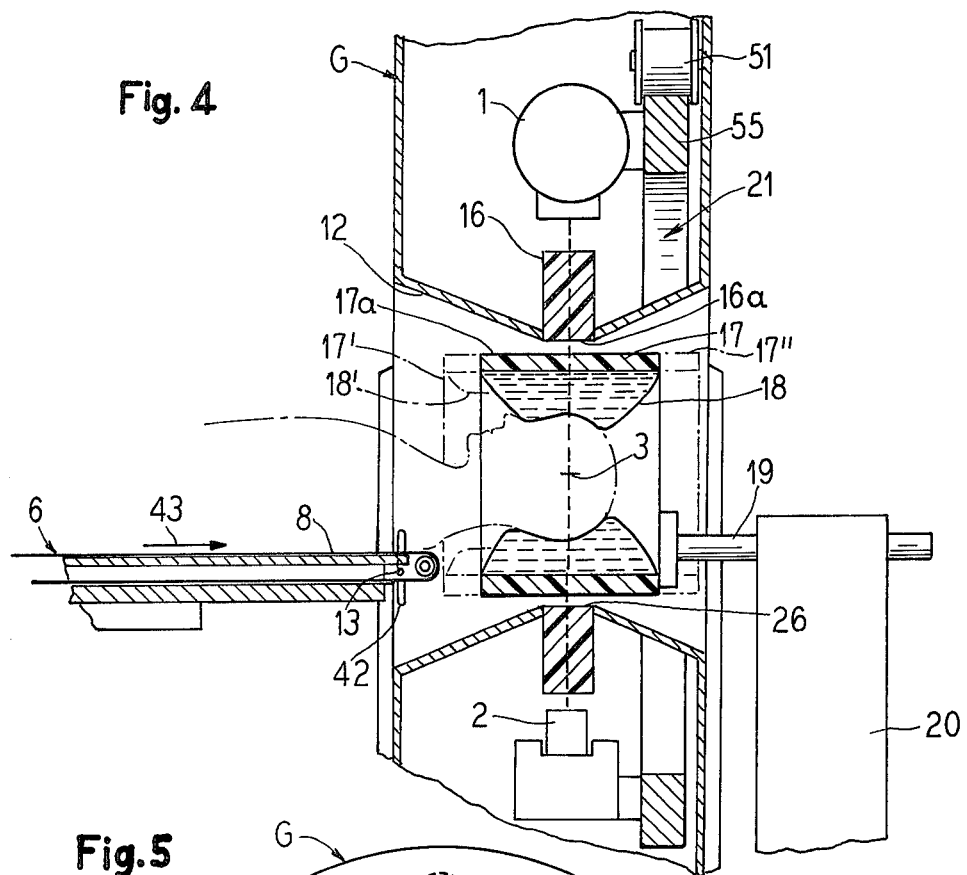
FIG. 4 is a partial longitudinal sectional view showing details of the medical examining apparatus according to the present invention when arranged for receiving and supporting the patient's head within the through-aperture of the apparatus.

For making a cranial examination, the parts are arranged as shown in FIGS. 4 and 5 with the patient holder 17, 18 disposed at a position such as indicated in dot-dash outline in FIG. 4 and as designated by reference numerals 17' and 18'. With the illustrated embodiment, the contouring member 18 may be assumed to be of an elastic material which tends to constrict into a position closely adjacent the inner surface of the ring 17. With the member 18 partially filled with a suitable liquid such as water, as shown in FIG. 1, for example, the inner diameter of the member 18 exceeds a maximum head dimension to be received thereby, and the surface such as indicated at 18a in FIG. 1 lies in a generally cylindrical form coinciding with the level of the roll cloth 8. Thus, with the patient completely supported on patient support 6, the support 6 may be locked at the position shown in FIG. 4 by means of the pins 13 engaging in slots such as indicated at 42, and the motor 10 may be activated to advance the patient toward the aperture 12. The supporting structure 20 may be suitably locked in the position shown in FIG. 4 for example by locking the casters 41 against rotation and thereby preventing relative movement of the structure 20 with respect to the floor 42. Similarly, the rods 19 may be momentarily locked against longitudinal movement by a suitable braking means during transfer of the patient's head from the roll cloth 8 to the contouring member 18 of holder 17. Thus, the patient's head may be transferred to the holder 17 without any manual assistance or with a minimum of manual assistance and with no substantial physical exertion required on the part of the attendant.

With the patient's head transferred to the holder and the holder in the position indicated at 17', 18' the contouring member 18 may be filled with liquid to the extent desired so as to ensure that the member 18 is in conforming contact with the patient's head and is firmly located relative thereto. Any brake associated with the rods 19 is now released. The motor 10 is now activated to advance the roll cloth 8 in the direction of arrow 43 so as to move the holder from the initial position 17', 18' to a selected operating position such as that shown in solid sectional outline in FIG. 4. The range of adjustment which would be comfortable to the patient is indicated as including an extreme right-hand position 17" in FIG. 4, the range between position 17' and position 17" preferably substantially corresponding to the range of possible medical interest utilizing the particular contouring configuration of the holder 17. The apparatus is such, however, that a holder with contouring member of different size or different configuration can be readily substituted should this prove desirable.

So as to further minimize the necessary amount of patient handling, the housing G is shown as being mounted on a fulcrum 45 carried at the floor 42. Trunnions are indicated at 46 and 47 which allow for pivotal movement of the measuring apparatus 1, 2 together with its ring 55 in the general plane of FIG. 4 for the sake of selecting a precise transverse section to be examined. It will be noted from FIG. 4 that the housing G and associated parts are particularly free for clockwise rotation about a pivot axis which includes central point 3 in FIG. 4. Thus, should pivot movement in the opposite direction be desired the supporting structure 20 could be replaced by a similar structure directly mounted to the fulcrum 45 and extending horizontally at the level of rods 19 for supporting the longitudinal reciprocation thereof without interfering with the full range of pivotal movement of the housing G relative to the trunnions 46, 47. When the desired exact patient position is achieved, the rods 19 may be again braked, should this be desirable.

When the examination was complete, any braking of the rods 19 would be released, and the motor 10 energized to drive roll cloth 8 in the direction opposite to arrow 43 to return the holder 17, 18 to the initial position 17', 18'. The liquid in the contouring member 18 would now be drained off until the contouring member 18 resumed its initial configuration such as indicated in FIG. 1. Further activation of the motor 10 with minimum manual assistance to the patient would then return the patient completely to the patient's support 6, and allow the patient to be removed from the aperture 12, for example by release of the pins 13 and translational movement of the patient's support 6.

The described apparatus is suitable both for whole body examinations and for cranial examinations with the use of a contouring member such as 18. For such cranial examinations, there is provided a holder assembly 17, 18, 19 provided with a suitable supporting structure such as 20 greatly facilitating the movement of the patient in a comfortable and convenient manner into the operative position. For maximum simplicity and flexibility, the support structure 20 is preferably movably supported on the floor itself so as to avoid encumbering the apparatus in any way during whole body examination. Similarly, the couch or patient's support 7 is movably supported on the floor so as to be conveniently completely retracted from the housing aperture 12 during cranial examination.

Summary Of Operation

In operation of the apparatus of FIG. 1 for cranial examination, the couch 7 is, of course, retracted from the housing aperture 12, so that the apparatus 17-20 can take its place. The couch 7 is released by manipulation of the handle H so as to remove the pins 14 from the associated slots. The apparatus 17-20 is then moved to a position such as shown in FIG. 4 and suitably locked in position for example by applying brakes to the casters 41. With the contouring member 18 partly filled with liquid, for example, as shown in FIG. 1, the inner surface of member 18 as indicated at 18a will have a cylindrical configuration and may have a lower surface essentially level with the roll cloth 8, FIG. 4. The holder assembly 17, 18, 19 is then displaced to the extreme position indicated at 17', 18' in FIG. 4 so as to have a minimum gap from the end of the roll cloth 8 and so as to comfortably receive the head of the patient as the roll cloth 8 is advanced in the direction of arrow 43 by means of the motor 10, FIG. 1. Thus, the head of the patient can be transferred to the central part of the contouring member 18' with a minimum of manual assistance by an attendant and with essentially negligible effort. Once the patient's head is properly located on the contouring member 18', the contouring member is filled with water to the desired extent such that the surface of the contouring member 18 conforms with the patient's head over the entire range of possible examination. As shown in solid sectional outline in FIG. 4, with this degree of filling of the contouring member 18, the contouring member 18 conforms with the back of the patient's head to such an extent as to essentially firmly associate the patient's head with the holder assembly 17-19.

Once such firm association with the holder assembly is established, the patient may be moved by means of the motor 10 and roll cloth 8 and the holder assembly 17-19 will comfortably and securely support the patient's head during any adjustment over the range between the extreme positions indicated at 17', 18' on the left and 17" on the right, FIG. 4. The range of adjustment preferably corresponds to the range of medical interest for the given holder configuration.

With the patient suitably located as indicated in solid sectional outline in FIG. 4, the housing G and the associated apparatus including X-ray tube 1 and receiver 2 may be tilted about trunnions 46, 47, FIG. 5, for further adjustment of the precise region to be examined without disturbance to the patient.

Having established the patient at the exact desired position relative to the measurement apparatus 1, 2, the scanning operation may begin with the measurement apparatus 1, 2 at an initial position, for example 90° counterclockwise from that shown in FIG. 5. After registration of the readings of each of the individual detectors indicated in FIG. 3, the measuring apparatus is displaced in the clockwise direction by a suitable small angular increment, and a further set of readings taken. By this procedure, a substantial number of sets of readings of the order of 90 or more may be taken very rapidly, for subsequent processing by computer 4 of FIG. 1 and reproduction on the display device 5.

When the scanning procedure is completed, the motor 10 is energized in the opposite direction so as to move the patient to the left as viewed in FIG. 4 and to return the holder assembly to the initial position 17', 18'. Thereafter, the water is drained from the contouring member 18 to the extent desired, and the motor 10 again energized to transfer the patient completely to the support 6. The entire support 6 may be released by means of retraction of the pins 13 from the slot 42 by manipulation of the handle 15 shown in FIG. 2.

If desired, it will be understood that the slots such as 42 may be arcuately elongated with a center at 3, FIG. 4 so that the pivotal adjustment of the housing G about the trunnions 46, 47 can take place without producing any relative movement of the patient support means 6, 17-19. With the illustrated embodiment, it is contemplated that only relatively very small pivotal adjustments of the housing G will be desired during cranial examination.

As indicated in FIG. 2, the floor surface 42 may be provided with grooves 42a, 42b, or similar guideways for guiding the movement of support structure 20 between its operative and inoperative positions and for facilitating the precise positioning of the holder 17-19 in its operative relationship as shown in FIG. 4.

Reference To Related Disclosure

Further preferred details of the system for maintaining suitable liquid pressure and temperature within the contouring member 18 may be obtained by reference to the commonly assigned pending application Ser. No. 601,706 filed Aug. 4, 1975. This disclosure will also illustrate an alternative configuration for the contouring member 18 wherein the contouring member initially has an inner diameter smaller than the smallest head dimension to be accommodated. With this type of contouring member, the liquid control system of the prior application is particularly advantageous since such system enables the creation of a partial vacuum interiorly of the contouring member so as to retract the member to a larger diameter prior to reception of the patient's head. This pending application also teaches that the contouring member 18 may be closed at one end so as to define a diameter at such end smaller than the smallest anticipated head dimension to be received. Such an arrangement facilitates the contouring of the member 18 at the top of the patient's head to any desired degree. It will be apparent from the disclosure of this prior application that the contouring member need not be completely symmetrical but may have a greater length at the lower side of the patient's head than at the upper side of the patient's head, and may be provided with internal webbing or straps so as to ensure that the contouring member such as 18 is clear of the patient's face proper including the eyes should this be desired. According to the teaching of the prior application, however, it is desirable to have a liquid return communicating with the uppermost part of the reservoir defined between the contouring member 18 and the associated ring 17 of tissue-equivalent density.

With the illustrated embodiment of FIGS. 4 and 5, there is a sufficient clearance between the external cylindrical surface 17a of the holder assembly and the interior cylindrical surface 16a of the compensating member 16 to accommodate about 15° of tilting adjustment in the clockwise direction as viewed in FIG. 4 about the pivot axis coincident with center point 3 and defined by trunnions 46, 47, FIG. 5. Where such a range of tilting adjustment of the measuring apparatus 1, 2 is not desired, the clearance between the surfaces 16a and 17a may be at a minimum to provide the necessary mechanical clearance for longitudinal movement of the holder assembly 17, 18, 19. Alternatively, the outer surface 17a may be contoured to have an arcuate external surface with a center of curvature at three such that the gap 26 between the surfaces 16a and 17a is at a minimum while still accommodating the desired range of tilting adjustment about trunnions 46, 47, and without a substantial change in the length of the ray path within the tissue-equivalent material 16, 17. In any event, it is also desirable that the ray path between source 1 and each detector of receiver 2 have essentially the same length in the tissue equivalent material 16, 17, in each of the angular positions of the ring 55 relative to the rollers 51-53.

The members 16 and 17 may be formed of rigid plastic material having tissue-equivalent density, for example acrylic glass. The opening 26 of the housing can have a diameter of about fifty centimeters (50 cm), for example, while the external diameter of ring 17 is somewhat smaller than the aperture diameter, for example forty-five centimeters (45 cm).

It will be apparent that many modifications and variations may be effected without departing from the scope of the novel concepts of the present invention.

I claim as my invention:

1. Medical examining apparatus for obtaining transverse sectional images, comprising a ray measuring arrangement for generating a bundle of rays which penetrate a body segment and which scan the region of a selected transverse section of such body segment over a sufficient number of angularly offset ray paths through the region so that radiation received during the scanning of the region can be converted into signals defining a sectional image, a housing containing a compensating body comprising tissue-equivalent material for forming part of the ray path and having a patient-receiving through-aperture such that a patient may be moved relative to the ray measuring arrangement for selecting the region to be scanned, and means comprising a patient support movable with respect to a longitudinal axis of such patient-receiving through-aperture operable for moving a patient into and through said through-aperture so as to align any desired body segment of the patient with the ray measuring arrangement, the improvement comprising a holder assembly having a contouring member for filling with a liquid medium so as to conform with and firmly engage the head of a patient, and a supporting structure for mounting the holder assembly within the patient-receiving through-aperture, said supporting structure accommodating the removal of the holder assembly out of said patient-receiving through-aperture to accommodate scanning of a body part of a patient more nearly approximating the size of said patient-receiving aperture.

2. Apparatus according to claim 1 with said supporting structure mounting said holder assembly for longitudinal movement axially of the patient-receiving through-aperture so as to accommodate adjustment of the patient relative to the measuring arrangement.

3. Apparatus according to claim 2 with said supporting structure providing substantially friction-free longitudinal displacement of the holder assembly.

4. Appartus according to claim 3 with said contouring member being of a generally annular configuration and of a length to engage the back of the head on both axial sides of a protuberance thereof such that the contouring member can be firmly associated with the head of a patient for joint axial movement in either direction without any relative slippage when the contouring member is suitably filled with a liquid medium.

* * * * *